(12) United States Patent
Ochiai et al.

(10) Patent No.: US 7,008,927 B2
(45) Date of Patent: Mar. 7, 2006

(54) PRALMORELIN-CONTAINING NASAL DROP PREPARATIONS

(75) Inventors: Akiko Ochiai, Shizuoka (JP); Yasutomi Kato, Shizuoka (JP); Hirokuni Kogetsu, Shizuoka (JP); Kiyoshi Maruyama, Shizuoka (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 333 days.

(21) Appl. No.: 10/296,791

(22) PCT Filed: May 29, 2001

(86) PCT No.: PCT/JP01/04503

§ 371 (c)(1),
(2), (4) Date: Nov. 26, 2002

(87) PCT Pub. No.: WO01/91782

PCT Pub. Date: Dec. 6, 2001

(65) Prior Publication Data

US 2003/0139347 A1    Jul. 24, 2003

(30) Foreign Application Priority Data

May 29, 2000   (JP)   .............................. 2000-158676

(51) Int. Cl.
*A61K 38/00*   (2006.01)

(52) U.S. Cl. ....................................... 514/17
(58) Field of Classification Search ................. 514/17
See application file for complete search history.

(56) References Cited

U.S. PATENT DOCUMENTS 5,776,901 A * 7/1998 Bowers et al. ................ 514/16
2004/0014671 A1 * 1/2004 Murata et al. ................ 514/17

FOREIGN PATENT DOCUMENTS

| EP | 080879 A | 6/1983 |
| EP | 0 301 392 | 2/1989 |
| EP | 490549 A | 6/1992 |
| EP | 724885 A | 8/1996 |
| JP | 63-303931 A | 12/1988 |
| JP | 7-278015 A | 10/1995 |
| JP | 10-45619 A | 2/1998 |
| WO | WO 99/62539 | 12/1999 |
| WO | WO 01/97831 | 12/2001 |

OTHER PUBLICATIONS

Johansen, P.B., et al (1998) Xenobiotica vol. 28, No. 11, p. 1083-1092.
Pihoker, C., et al (1997) J. Endocrinol. vol. 155, No. 1, pp. 79-86.
Pihoker, C., et al (1995) J. Clin. Endocrinol. Metabolism. vol. 80, No. 10, pp. 2987-2992.
Kaji, H., et al (1995) Hormone to Rinshou (Hormone and Clinic) vol. 43, No. 1, pp. 57-60 (with a partial English translation).
Vora, J., et al (1993) Journal of Controlled Release vol. 24, pp. 193-200.
Chan, R., et al (1988) Clinical Pharmacology & Therapeutics 44(3) pp. 275-282.
Dua, R., et al (1997) International Journal of Pharmaceutics, 147(2) pp. 233-242.
Patent Abstracts of Japan, Publication No. 2002053489, published Feb. 19, 2002. Doi Naomi, "Muscle Pill/Medicine for Preventing/Treating Muscular Decay." .

* cited by examiner

*Primary Examiner*—Christopher R. Tate
*Assistant Examiner*—Maury Audet
(74) *Attorney, Agent, or Firm*—Nixon Peabody LLP

(57) ABSTRACT

The preparation for intranasal administration comprising D-alanyl-3-(naphthalen-2-yl)-D-alanyl-L-alanyl-L-tryptophyl-D-phenylalanyl-L-lysinamide (pralmorelin) and/or an acid addition salt thereof as an active ingredient and water permits a marked increase in the in vivo absorption of pralmorelin and hence provides adequate efficacy even if it is administered in a small dose at a time. The preparation also allows pralmorelin to be dissolved in an increased amount, so it can be formulated pharmaceutically with great ease. It also high stability over time.

14 Claims, No Drawings

PRALMORELIN-CONTAINING NASAL DROP PREPARATIONS

CROSS-REFERENCE TO RELATED APPLICATIONS

This application is a 371 National Phase Entry of co-pending International Application No. PCT/JP01/04503, filed May 29, 2001, which designated the U.S. and which claims the benefit under 35 U.S.C. § 119 of Japanese Application No. 158676/2000, filed May 29, 2000.

TECHNICAL FIELD

This invention relates to preparations for intranasal administration containing D-alanyl-3-(naphthalen-2-yl)-D-alanyl-L-alanyl-L-tryptophyl-D-phenylalanyl-L-lysinamide (hereunder sometimes abbreviated as pralmorelin) which is a kind of growth-hormone releasing peptide (hereunder sometimes abbreviated as GHRP). More specifically, the invention relates to a formulation that increases the in vivo absorption of pralmorelin, as well as a preparation for intranasal administration of pralmorelin that enables increasing the concentration of pralmorelin in the preparation.

BACKGROUND ART

The secretion of growth hormone is known to be regulated by a growth-hormone releasing factor in the hypothalamus and a growth-hormone release inhibiting factor somatostatin. In the case of humans, the growth-hormone releasing factor (hereunder sometimes abbreviated as GHRH) in the hypothalamus is a peptide having about 40 amino acid residues and several types including one separated and purified from human cells and one synthesized with a peptide synthesizer have begun to be used as an in vivo diagnostic or a therapeutic of dwarfism. However, the method involving separation and purification from human cells has the problem of limited productivity whereas the synthesis method which requires condensation of almost 40 amino acids is not only cumbersome in operation but also time-consuming and less cost-effective.

Development and research has therefore been made of peptides that consist of a shorter chain of amino acids, that are easy to synthesize and that promote the secretion of growth hormone. As a result, growth-hormone releasing peptides such as pralmorelin have been developed as therapeutics of hypothalamic or pituitary dwarfism or diagnostics of pituitary functions (JP 7-507039 A (Kohyo) and JP 10-45619 A (Kokai)).

It has been known that those growth-hormone releasing peptides (GHRPs) share no structural homology with GHRH but that their effects on the release of growth hormone are similar, except for the mechanism of actions they exhibit. A recent report also discloses that whereas GHRH has only direct action on the secretion of growth hormone in the pituitary, GHRPs not only directly affect the secretion of growth hormone in the pituitary but also show GHRH secreting action in the arcuate nucleus and somatostatin secretion inhibiting action in the periventricular nucleus.

Thus, because of these differences in structure and mechanism of action, there is a need to study the method of applying GHRPs such as pralmorelin aside from the application method for GHRH. In the past, pralmorelin has primarily been administered as an injection. However, there is a demand for the development of preparations that impose less stress on patients and pralmorelin has recently been shown to be effective in intranasal administration (Journal of Clinical Endocrinology and Metabolism, Vol. 80, No. 10, pp. 2987–2992 (1995), Journal of Endocrinology, 155, pp. 79–86 (1997) and Xenobiotica, Vol. 28, No. 11, 1083–1092 (1998)).

The reported preparations for intranasal administration use physiological saline as a solvent. This is because the preparations for intranasal administration which are applied to the nasal mucosa are commonly rendered isotonic with physiological saline in order to reduce irritation. However, in the case of pralmorelin, the use of physiological saline as a solvent presents the following problems and it is difficult to formulate it pharmaceutically.

To be more specific, pralmorelin has low saturated solubility in physiological saline (0.15 w/v % at 25° C. when it is dihydrochloride) and at higher concentrations, pralmorelin becomes insoluble with the lapse of time and a problem occurs in terms of storage stability, thus making it difficult to formulate pralmorelin pharmaceutically using physiological saline. Even at concentrations lower than its saturated solubility, pralmorelin has low in vivo absorption and needs frequent administration.

Hence, no pralmorelin preparations have ever been made practicable using physiological saline.

In view of these, in order to develop pralmorelin preparations for intranasal administration, it is essential to increase the absorption and concentration of pralmorelin in the preparation and there is an urgent need to develop preparations that are improved in those aspects. It is also indispensable to provide pralmorelin preparations for intranasal administration that ensure high stability over time in practical applications.

An object, therefore, of the invention is to increase the in vivo absorption of pralmorelin.

Another object of the invention is to provide a pralmorelin preparation for intranasal administration having higher concentration than preparations using physiological saline. Since inorganic salts formerly used as osmolarity moderators lower the solubility of pralmorelin, the present inventors made intensive studies including the choice of useful osmolarity moderators other than the inorganic salts.

Still another object of the invention is to obtain industrially feasible pralmorelin containing preparations for intranasal administration and to design practically feasible formulations.

DISCLOSURE OF THE INVENTION

Under the above-described circumstances, the present inventors took to working on pralmorelin preparations for intranasal administration and made various studies. As a result, they found that preparations comprising water and pralmorelin and/or acid addition salts thereof (preferably water and acid addition salts of pralmorelin) without using heretofore common physiological saline achieved higher in vivo absorption of pralmorelin and higher solubility of pralmorelin than when physiological saline was used, thus assuring better stability over time as preparations. It was also found that pralmorelin preparations for intranasal administration which were rendered isotonic with at least one osmolarity moderator selected from non-electrolytes such as sugar alcohols, sugars and alcohols achieved higher absorption of pralmorelin than preparations that were rendered isotonic with physiological saline. The inventors also found that when such osmolarity moderators were incorporated, the absorption of pralmorelin increased at low osmotic pressure. Furthermore, as regards the relationship between the concentration of pralmorelin in the preparation of the invention for intranasal administration and the in vivo absorption of pralmorelin, the inventors found that the in vivo absorption of pralmorelin increased markedly as its concentration increased. Therefore, the preparation of the invention brings about adequate efficacy even if the dose of pralmorelin administered at a time is smaller than in the case of the conventional preparations using physiological saline. In short, the present inventors found practically feasible pralmorelin preparations for intranasal administration featuring improved absorption of pralmorelin.

Hence, the present invention provides a preparation for intranasal administration comprising D-alanyl-3-(naphthalen-2-yl)-D-alanyl-L-alanyl-L-tryptophyl-D-phenylalanyl-L-lysinamide and/or an acid addition salt thereof as an active ingredient, and water.

BEST MODE FOR CARRYING OUT THE INVENTION

The following are preferred embodiments of the invention.

According to an embodiment of the invention, there is provided a preparation for intranasal administration consisting essentially of D-alanyl-3-(naphthalen-2-yl)-D-alanyl-L-alanyl-L-tryptophyl-D-phenylalanyl-L-lysinamide and/or an acid addition salt thereof as an active ingredient, and water.

According to another embodiment of the invention, there is provided the above-described preparation for intranasal administration, in which the active ingredient is an acid addition salt of D-alanyl-3-(naphthalen-2-yl)-D-alanyl-L-alanyl-L-tryptophyl-D-phenylalanyl-L-lysinamide.

According to another embodiment of the invention, there is provided the above-described preparation for intranasal administration, in which the acid addition salt is hydrochloride.

According to another embodiment of the invention, there is provided the above-described preparation for intranasal administration, in which the active ingredient is D-alanyl-3-(naphthalen-2-yl)-D-alanyl-L-alanyl-L-tryptophyl-D-phenylalanyl-L-lysinamide dihydrochloride.

According to another embodiment of the invention, there is provided the above-described preparation for intranasal administration, which further contains a non-electrolyte.

According to another embodiment of the invention, there is provided the above-described preparation for intranasal administration, in which the non-electrolyte is at least one member of the group consisting of sugar alcohols, sugars and alcohols.

According to another embodiment of the invention, there is provided the above-described preparation for intranasal administration which has an osmolarity ratio of not more than about 1.

According to another embodiment of the invention, there is provided the above-described preparation for intranasal administration which has an osmolarity ratio of from not less than about 0.01 to not more than about 0.5.

According to another embodiment of the invention, there is provided the above-described preparation for intranasal administration which further contains at least one antiseptic selected from quaternary ammonium salts and parabens.

According to another embodiment of the invention, there is provided the above-described preparation for intranasal administration, in which the concentration of the active ingredient is from about 0.05 to about 1.5 w/v %.

According to another embodiment of the invention, there is provided the above-described preparation for intranasal administration which has a pH of from about 4 to about 7.

According to another embodiment of the invention, there is provided the above-described preparation for intranasal administration which is a sprayable solution.

Acid addition salts of pralmorelin are used more preferably than its free form in view of the solubility of pralmorelin. Examples of acids that can form acid addition salts include inorganic acids such as hydrochloric acid, sulfuric acid, hydrobromic acid, phosphoric acid and nitric acid, organic acids such as formic acid, acetic acid, propionic acid, succinic acid, glycolic acid, lactic acid, malic acid, tartaric acid, citric acid, maleic acid, phthalic acid, phenylacetic acid, benzoic acid, salicylic acid, methanesulfonic acid, toluenesulfonic acid, benzenesulfonic acid, oxalic acid and trifluoroacetic acid, and amino acids such as aspartic acid and glutamic acid. Among these acids, those which can form pharmaceutically acceptable acid addition salts are chosen as appropriate.

Preferred acid addition salts are hydrochlorides and dihydrochlorides are more preferred.

The preparations of the invention may employ pralmorelin in combination with one or more acid addition salts thereof.

As used in the preparations of the invention, "water" means any water that is conventionally used in pharmaceutical formulating of medicines as exemplified by tap water, distilled water and purified water; distilled water and purified water are preferred.

For the preparations of the invention, the combination of pralmorelin and/or acid addition salts thereof with water is the most preferred from the viewpoint of in vivo absorption of pralmorelin. If desired, auxiliary agents such as osmolarity moderators, preservatives and dispersants may be employed. As already mentioned, the preparations of the invention should not contain inorganic salts at 0.9 w/v % or higher concentrations which are common in physiological saline because absorption of pralmorelin is impaired; it should however be noted that very small amounts of inorganic salts may be contained.

Osmolarity moderators that may be employed in the preparations of the invention are those which are commonly used as isotonization agents in pharmaceuticals; from the viewpoints of solubility and in vivo absorption, they are preferably non-electrolytes as exemplified by sugar alcohols, sugars and alcohols; one or more of these non-electrolytic osmolarity agents may be used.

Sugar alcohols encompass not only straight polyhydric alcohols obtained by reducing the carbonyl groups in sugar but also cyclic alcohols; examples include D-mannitol, xylitol, galactitol, glucitol, inositol, D-sorbitol, etc. and preferred examples include D-manntiol, xylitol and D-sorbitol. Alcohols include glycerin.

Sugars encompass monosaccharides, oligosaccharides and polysaccharides; examples include glucose, fructose, sucrose, maltose and lactose and preferred examples include glucose, fructose, sucrose and maltose.

If an additive, in particular, an osmolarity moderator, is used in the pralmorelin preparation of the invention for intranasal administration, its content is preferably the smaller from the viewpoint of pralmorelin absorption and the osmolarity ratio is preferably about 1.2 or less, more preferably about 1 or less, even more preferably about 0.8 or less, and most preferably between about 0.01 and about 0.5. The term "osmolarity ratio" as used in the invention is expressed by a relative ratio based on physiological osmotic pressure. Stated specifically, it means an osmolarity ratio as determined by calculation for the concentration of sodium chloride, with the osmolarity ratio of an aqueous solution of 0.9 w/v % sodium chloride being taken as 1. Even if an osmolarity ratio of 1 is obtained by using one of the non-electrolytic osmolarity moderators listed above, the in vivo absorption of pralmorelin can be increased compared to the case of obtaining isotonicity with sodium chloride and this has been verified in the experiments to be described later.

Antiseptics that can be used in the invention include quaternary ammonium salts such as benzalkonium chloride and benzethonium chloride, as well as parabens including methyl paraoxybenzoate, ethyl paraoxybenzoate, propyl paraoxybenzoate, butyl paraoxybenzoate, etc. One or more of these ingredients may be used in the invention.

Pralmorelin or salts thereof may be incorporated in the preparations in such amounts that their concentration is preferably about 0.05 w/v % upward, more preferably between about 0.05 and about 1.5 w/v %, even more preferably between about 0.05 and about 0.30 w/v %, and most preferably between about 0.05 and about 0.15 w/v %. More preferred are pralmorelin preparations for intranasal administration that are adjusted to have pH between about 4 and about 7.

The preparations of the invention may be administered at doses that can be adjusted as appropriate for the severity of the disease, the age of the patient, his or her body weight and the symptom manifested. For a single administration, the dose is preferably between about 0.1 and about 100 μg per kg of body weight, more preferably between about 0.5 and about 10 μg per kg of body weight, if pralmorelin dihydrochloride is to be administered. The preparations of the invention are preferably administered once to four times daily and a single dosage may be applied to one or both nostrils. For a single administration, the volume is preferably between about 50 and about 200 μl per nostril, more preferably about 100 μl per nostril.

The preparations of the invention may take any form without particular limitations and ordinary forms may be adopted that are conventional to preparations for intranasal administration, as exemplified by drops, sprayable solutions (e.g. liquids and aerosols that can be sprayed with nebulizers), washes, infusions, etc. From the viewpoint of convenience in handling, the preferred form is such that the preparation is contained in a vessel that needs to be pushed once to release a predetermined amount of the active ingredient. In the case of sprayable solutions, particles sprayed preferably have an average size between about 30 and about 70 μm.

The following preparations and examples are provided for the purpose of further illustrating the present invention but are in no way to be taken as limiting.

Preparations

Preparations for intranasal administration that contained 0.1 w/v % pralmorelin were formulated using distilled water as a solvent, pralmorelin dihydrochloride as the active ingredient (it was prepared by the method described in JP 7-507039 A (kohyo) and the same compound was used in the following examples), and benzalkonium chloride as an antiseptic (Table 1). The preparations were measured for pH and osmolarity ratio in accordance with General Test Methods in the Japanese Pharmacopoeia (Table 1).

TABLE 1

| Concentration of pralmorelin (w/v %) | Concentration of additive (w/v %) | pH | Osmolarity Ratio |
|---|---|---|---|
| 0.1 | benzalkonium chloride (0.005) | 5.7 | 0.02 |
| 0.1 | benzalkonium chloride (0.01) | 5.8 | 0.02 |

Benzalkonium chloride (50 w/v % conc. sol.): product of Maruishi Pharmaceutical Co., Ltd.

The average particle size of each preparation for its use as a sprayable solution was measured as follows. The preparation shown in Table 1 which contained 0.1% (w/v) of pralmorelin dihydrochloride and 0.005% (w/v) of benzalkonium chloride was sprayed with a nebulizer for intranasal administration (New Nosuran bottle with a capacity of 10 ml; product of Shinko Kagaku K.K.) and subjected to measurement of average particle size with a particle size analyzer operating on the scattering of laser light (Model LDSA-1400A; product of Tonichi Computer Applications); the result was 65 μm.

EXAMPLE 1

With an isotonic solution (in distilled water) of 5 w/v % D-mannitol or physiological saline used as a solvent, a solution of 0.1 w/v % pralmorelin dihydrochloride was prepared and administered to male rats (7-week old, Crj:CD (SD) strain, N=3) in an amount of 50 μg/kg.

With the rats fixed supine under an unanesthetized condition, the pralmorelin solution was administered into one nostril of each rat in an amount of 50 μg/kg with a micropipette. The rats were not anesthetized for two reasons: actual drug administration is effected without anesthesia; the effects anesthetization would have on drug absorption have not been elucidated.

The concentration of an unchanged substance in plasma was measured in accordance with the two-antibody competition method of Kitagawa et al. summarized below [J. Assoc. Off. Anal. Chem., Vol. 68, No. 4, pp. 661–664 (1985) and J. Immunological Methods, 72, pp. 109–118 (1984)].

Anti-rabbit IgG goat IgG (Jackson Immuno Research) as the second antibody was adsorbed on an ELISA 96-well microplate (GREINER). Then, anti-pralmorelin dihydrochloride rabbit serum was adsorbed on the same microplate; the serum was the first antibody and had been obtained by subcutaneous injection of rabbits with an immunogen having pralmorelin dihydrochloride bound to bovine serum albumin (Sigma) by means of water-soluble carbodiimide (Nakarai Tesk).

Pralmorelin dihydrochloride contained in a sample was allowed to compete for pralmorelin labeled β-galactosidase that had been crosslinked with crosslinker N-(m-maleimidebenzoyloxy)succinimide (Nakaral Tesk); then, the β-galactosidase bound to the first antibody was reacted with 4-methylumbelliferyl-β-D-galactopyranoside; thereafter, the enzymatic activity of the β-galactosidase bound to the first antibody was measured at an excitation wavelength of 370 nm and a fluorescence wavelength of 460 nm.

From the measured values for the enzymatic activity of the β-galactosidase, the maximum plasma drug concentration (Cmax) of pralmorelin dihydrochloride, the area under the plasma drug concentration vs time curve (AUC) and the bioavailability (the ratio of AUC obtained by intranasal administration to AUC obtained by intravenous administration) were obtained.

As a result, it was found that the solution for intranasal administration that had been rendered isotonic with mannitol was more readily absorbed in vivo than the one rendered isotonic with physiological saline (Table 2).

TABLE 2

Comparison of two solvents, physiological saline and 5 w/v % D-mannitol

|  | Cmax (ng/ml) | AUC (ng · hr/ml) | Bioavailability (%) |
|---|---|---|---|
| Physiological saline | 0.70 | 1.98 | 3.08 |
| 5% D-mannitol | 2.37 | 2.71 | 4.22 |

EXAMPLE 2

A preparation for intranasal administration containing 0.3 w/v % pralmorelin was prepared using distilled water as a solvent, pralmorelin dihydrochloride as the active ingredient and benzalkonium chloride as an antiseptic (Table 3). Another preparation for intranasal administration containing 0.3 w/v % pralmorelin was prepared in the same manner except that it further contained D-mannitol as an osmolarity moderator (Table 4). The two preparations were filled into glass ampules and each stored at 50° C. and 60° C. under light-tight conditions for 2 weeks. Initially and after 2 weeks, each solution was checked for the appearance, pH, osmolarity ratio, pralmorelin content (residual) and purity (Tables 5 and 6). The appearance of each solution was observed in accordance with General Rule 21 in the 13$^{th}$ Revised Japanese Pharmacopoeia. Measurements of pH and osmolarity ratio were conducted in accordance with General Test Methods in the Japanese Pharmacopoeia. Measurements of pralmorelin content and purity were conducted by liquid chromatography.

As a result, it became clear that whether D-mannitol was contained or not, the use of pralmorelin and distilled water enabled the making of preparations for intranasal administration that contained pralmorelin at a concentration of 0.3 w/v % which was higher than 0.15 w/v % (25° C.), i.e., the saturated solubility in physiological saline. The preparations had high stability over time.

TABLE 3

Ingredients and their contents in pralmorelin preparation for intranasal administration

| Ingredient | Content (w/v %) |
|---|---|
| Pralmorelin dihydrochloride | 0.3 |
| Benzalkonium chloride | 0.01 |
| Distilled water | q.s. |

TABLE 4

Ingredients and their contents in pralmorelin preparation for intranasal administration containing D-mannitol

| Ingredient | Content (w/v %) |
|---|---|
| Pralmorelin dihydrochloride | 0.3 |
| D-mannitol | 5 |
| Benzalkonium chloride | 0.01 |
| Distilled water | q.s. |

D-mannitol: product of Kyowa Hakko Kogyo Co., Ltd.
Benzalkonium chloride (50 w/v % conc. sol.): product of Maruishi Pharmaceutical Co., Ltd.

TABLE 5

Stability of pralmorelin preparation for intranasal administration

| Parameter | Initial | 50° C. × 2 wk | 60° C. × 2 wk |
|---|---|---|---|
| Appearance | colorless and clear liquid | colorless and clear liquid | colorless and clear liquid |
| pH | 5.05 | 5.63 | 5.72 |
| Osmolarity ratio | 0.03 | 0.03 | 0.03 |
| Content (%) | 100 | 100 | 99.3 |
| Purity (%) | 99.0 | 98.8 | 98.3 |

TABLE 6

Stability of pralmorelin preparation for intranasal administration containing D-mannitol

| Parameter | Initial | 50° C. × 2 wk | 60° C. × 2 wk |
|---|---|---|---|
| Appearance | colorless and clear liquid | colorless and clear liquid | colorless and clear liquid |
| pH | 5.35 | 5.67 | 5.52 |
| Osmolarity ratio | 1.05 | 1.05 | 1.04 |
| Content (%) | 100 | 100 | 99.3 |
| Purity (%) | 99.0 | 98.4 | 98.4 |

EXAMPLE 3

Since it was found to be possible to use D-mannitol as an osmolarity moderator, a test was made to check whether formulations would be feasible using other non-electrolytic osmolarity moderators.

Pralmorelin dihydrochloride (0.3 g) and D-mannitol (5 g) were dissolved in purified water (ca. 90 mL); after adding 1 mL of a solution containing 50 w/v % benzalkonium chloride, purified water was added to make 100 mL; the resulting solution was filtered to make a preparation for intranasal administration of pralmorelin (pralmorelin dihydrochloride, 0.3 w/v %; D-mannitol, 5 w/v %; benzalkonium chloride, 0.5 w/v %).

With this method used as a basic technique, pralmorelin preparations for intranasal administration were made according to the formulations shown in Table 7 and measured for pH and osmolarity ratio by the same methods as in Example 1.

As a result, it became clear that the use of non-electrolytic osmolarity moderators other than D-mannitol enabled the making of preparations for intranasal administration that contained pralmorelin at a concentration of 0.3 w/v % which was higher than 0.15 w/v % (25° C.), i.e., the saturated solubility in physiological saline.

TABLE 7

Pralmorelin preparations for intranasal administration containing various non-electrolytes

| Concentration of pralmorelin (w/v %) | Concentrations of additives (w/v %) | | pH | Osmolarity ratio |
|---|---|---|---|---|
| 0.3 | D-mannitol | (5) | 5.6 | 1.0 |
|  | benzalkonium chloride | (0.5) |  |  |
| 0.3 | xylitol | (5) | 5.7 | 1.2 |
|  | benzalkonium chloride | (0.5) |  |  |
| 0.3 | glucose | (5) | 5.4 | 1.0 |
|  | benzalkonium chloride | (0.5) |  |  |
| 0.3 | fructose | (5) | 5.7 | 1.0 |
|  | benzalkonium chloride | (0.5) |  |  |
| 0.3 | D-sorbitol | (5) | 5.5 | 1.0 |
|  | benzalkonium chloride | (0.5) |  |  |
| 0.3 | sucrose | (9.3) | 5.6 | 1.0 |
|  | benzalkonium chloride | (0.5) |  |  |
| 0.3 | glycerin | (2.6) | 5.6 | 1.1 |
|  | benzalkonium chloride | (0.5) |  |  |
| 0.3 | maltose | (10) | 5.2 | 1.0 |
|  | benzalkonium chloride | (0.5) |  |  |
| 0.3 | D-mannitol | (2.5) | 5.6 | 0.5 |
|  | benzalkonium chloride | (0.5) |  |  |
| 0.3 | D-mannitol | (1.5) | 5.7 | 0.3 |
|  | benzalkonium chloride | (0.5) |  |  |

D-mannitol: product of Kyowa Hakko Kogyo Co., Ltd.
Benzalkonium chloride (50 w/v % conc. sol.): product of Maruishi Pharmaceutical Co., Ltd.
Xylitol: product of Wako Pure Chemical Industries, Ltd.
Glucose: product of Otsuka Pharmaceutical Co., Ltd.
Fructose: product of Wako Pure Chemical Industries, Ltd.
D-sorbitol: product of Junsei Pure Chemical Co., Ltd.
Sucrose: product of Sanko Seiyaku Kogyo K.K.
Glycerin: product of Wako Pure Chemical Industries, Ltd.
Maltose (monohydrate): product of Wako Pure Chemical Industries, Ltd.

EXAMPLE 4

Two kinds of preparation for intranasal administration, one consisting of pralmorelin dihydrochloride and distilled water and the other further containing D-mannitol at varying concentrations, were evaluated for their effects on in vivo absorption of pralmorelin dihydrochloride. With four kinds of solvent, distilled water, 2.5 w/v % D-mannitol solution (osmolarity ratio, 0.5), 5 w/v % D-mannitol solution (osmolarity ratio, 1), 10 w/v % D-mannitol solution (osmolarity ratio, 2), solutions of 0.4 w/v % pralmorelin dihydrochloride were prepared and administered in an amount of 50 μg/kg to male rats as in Example 1. As a result, the following two observations were obtained: the highest absorption of pralmorelin was exhibited by the preparation for intranasal administration that consisted of pralmorelin dihydrochloride and distilled water; when D-mannitol was added, the in vivo absorption of pralmorelin dihydrochloride improved as the solution contained less D-mannitol, or became hypotonic.

Conventionally, absorption promoters such as surfactants were added to physiological saline in order to enhance the absorption of preparations for intranasal administration. However, it was verified that the preparation for intranasal administration which contained only distilled water besides pralmorelin dihydrochloride exhibited very high absorption of the active ingredient even when no absorption enhancer was used; it was also verified that even when a non-electrolytic osmolarity moderator was used, the in vivo absorption of pralmorelin dihydrochloride could be increased by just reducing the concentration of the non-electrolytic osmolarity moderator to render the solution hypotonic (Table 8).

TABLE 8

Bioavailability with distilled water or D-mannitol at concentrations of 2.5, 5 and 10%

|  | Cmax (ng/ml) | Bioavailability (%) |
|---|---|---|
| Distilled water | 60.7 | 26.2 |
| D-mannitol 2.5 (w/v %) | 55.8 | 22.1 |
| D-mannitol 5 (w/v %) | 49.2 | 19 |
| D-mannitol 10 (w/v %) | 21.7 | 9 |

EXAMPLE 5

With an aqueous solution of 0.005 w/v % benzalkonium chloride used as a base, pralmorelin preparations for intranasal administration were made at three concentrations, 0.1 w/v %, 0.3 w/v % and 1.0 w/v %, of pralmorelin dihydrochloride. Each preparation was dripped into the right nostril of 5-week old male Crj:CD (SD) rats (N=3). The dose of administration was 0.1 mg/kg, 0.3 mg/kg and 1.0 mg/kg for the respective preparations, which were all administered in a volume of 0.1 ml/kg.

As a result, it was found that when the same volume of pralmorelin dihydrochloride was administered intranasally, an increase in the concentration of pralmorelin in the administered solution allowed the in vivo absorption of pralmorelin to increase markedly beyond the value anticipated from the proportional relationship with its concentration (Table 9).

TABLE 9

| Dose (mg/kg) | Tmax (hr) | Cmax (ng/ml) | AUC (ng · hr/ml) |
|---|---|---|---|
| 0.1 | 0.17 | 18.04 | 14.54 |
| 0.3 | 0.17 | 72.85 | 48.14 |
| 1.0 | 0.17 | 501.83 | 250.05 |

(In the table, Tmax represents the time to the showing of maximum plasma concentration.)

INDUSTRIAL APPLICABILITY

The preparations of the invention for intranasal administration that comprise water and pralmorelin or acid addition salts thereof (preferably water and acid addition salts of pralmorelin) achieve better in vivo absorption of pralmorelin than the conventional preparations using physiological saline and an increase in the concentration of pralmorelin in the preparations for intranasal administration allows the in vivo absorption of pralmorelin to increase markedly beyond the value anticipated from the proportional relationship with its concentration. Therefore, compared to the conventional preparations using physiological saline, the preparations of the invention achieve adequate efficacy even if the dose of pralmorelin administered at a time is small. In addition, compared to the conventional preparations using physiological saline, the preparations of the invention for intranasal administration permit pralmorelin to be dissolved in an increased amount and, hence, can be formulated pharmaceutically with great ease. Further, the preparations of the invention for intranasal administration have very high stability over time as pharmaceutical products. As a result of these advantages, the present invention enables the production of practically feasible pralmorelin preparations for intranasal administration that have a simple enough formulation.

What is claimed is:

1. A preparation for intranasal administration which comprises D-alanyl-3-(naphthalen-2-yl)-D-alanyl-L-alanyl-L-tryptophyl-D-phenylalanyl-L-lysinamide and/or an acid addition salt thereof as an active ingredient, and water, and has an osmolarity ratio of from not less than 0.01 to not more than about 0.5.

2. The preparation for intranasal administration of claim 1 wherein said active ingredient is an acid addition salt of D-alanyl-3-(naphthalen-2-yl)-D-alanyl-L-alanyl-L-tryptophyl-D-phenylalanyl-L-lysinamide.

3. The preparation for intranasal administration according to claim 2, wherein said acid addition salt is hydrochloride.

4. The preparation for intranasal administration according to claim 3, wherein said active ingredient is D-alanyl-3-(naphthalen-2-yl)-D-alanyl-L-alanyl-L-tryptophyl-D-phenylalanyl-L-lysinamide dihydrochloride.

5. The preparation for intranasal administration according to claim 1, which further contains at least one antiseptic selected from quaternary ammonium salts and parabens.

6. The preparation for intranasal administration according to claim 1, wherein the concentration of said active ingredient is from about 0.05 to about 1.5 w/v %.

7. The preparation for intranasal administration according to claim 1, which has a pH of from about 4 to about 7.

8. The preparation for intranasal administration according to claim 1, which is a sprayable solution.

9. The preparation for intranasal administration according to claim 1, which further contains a non-electrolyte.

10. The preparation for intranasal administration according to claim 9, wherein the non-electrolyte is at least one member selected from the group consisting of sugar alcohols, sugars and alcohols.

11. The preparation for intranasal administration according to claim 9, which further contains at least one antiseptic selected from quaternary ammonium salts and parabens.

12. The preparation for intranasal administration according to claim 9, wherein the concentration of said active ingredient is from about 0.05 to about 1.5 w/v %.

13. The preparation for intranasal administration according to claim 9, which has a pH from about 4 to about 7.

14. The preparation for intranasal administration according to claim 9, which is a sprayable solution.

* * * * *